(12) United States Patent
Colonna et al.

(10) Patent No.: US 8,840,633 B2
(45) Date of Patent: Sep. 23, 2014

(54) FINGER ACTIVATED LANCET DEVICE

(75) Inventors: Robert Colonna, Newton, MA (US); Todd Taylor, Cambridge, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1590 days.

(21) Appl. No.: 11/400,042

(22) Filed: Apr. 7, 2006

(65) Prior Publication Data

US 2006/0264997 A1 Nov. 23, 2006

Related U.S. Application Data

(60) Provisional application No. 60/669,248, filed on Apr. 7, 2005.

(51) Int. Cl.
*A61B 17/32* (2006.01)
*A61B 5/151* (2006.01)
*A61B 5/15* (2006.01)

(52) U.S. Cl.
CPC ........... *A61B 5/1411* (2013.01); *A61B 5/15142* (2013.01)
USPC ........................................ 606/181

(58) Field of Classification Search
CPC ........... A61B 5/15142; A61B 5/15186; A61B 5/15146; A61B 5/14532; A61B 5/1411; A61B 17/32093
USPC ................... 606/181, 182; 600/583
See application file for complete search history.

(56) References Cited

U.S. PATENT DOCUMENTS

| 4,577,630 | A | * | 3/1986 | Nitzsche et al. | 606/182 |
| 4,715,374 | A | * | 12/1987 | Maggio | 606/182 |
| 4,844,095 | A | | 7/1989 | Chiodo et al. | |
| 4,869,249 | A | | 9/1989 | Crossman et al. | |
| 5,314,441 | A | * | 5/1994 | Cusack et al. | 606/182 |
| 5,366,470 | A | | 11/1994 | Ramel et al. | |
| 5,540,709 | A | * | 7/1996 | Ramel | 606/183 |
| 5,630,828 | A | | 5/1997 | Mawhirt et al. | |
| 5,755,733 | A | | 5/1998 | Morita | |
| 5,851,215 | A | * | 12/1998 | Mawhirt et al. | 606/181 |
| 6,136,013 | A | | 10/2000 | Marshall et al. | |
| 6,221,089 | B1 | * | 4/2001 | Mawhirt | 606/181 |
| 6,248,120 | B1 | | 6/2001 | Wyszogrodzki | |
| 6,322,574 | B1 | * | 11/2001 | Lloyd et al. | 606/181 |
| 6,432,120 | B1 | | 8/2002 | Teo | |
| 6,613,064 | B2 | * | 9/2003 | Rutynowski et al. | 606/185 |

(Continued)

FOREIGN PATENT DOCUMENTS

| GB | 2352403 A | 1/2001 | |
| WO | 03049613 A | 6/2003 | |
| WO | WO 03/049613 | * 6/2003 | A61B 5/15 |

*Primary Examiner* — Thomas McEvoy
*Assistant Examiner* — Julie A Szpira
(74) *Attorney, Agent, or Firm* — The Webb Law Firm

(57) ABSTRACT

A lancet device includes a housing with a cantilever spring extending therein and defining a lancet having a puncturing end on the cantilever spring. An actuator extends within the housing through an opening at the forward end. The actuator includes an interfering engagement with the cantilever spring. Movement of the actuator into the housing through the forward end pivots the cantilever spring against its relaxed condition and then releases the engagement with the cantilever spring, thereby permitting the cantilever spring to pivot the lancet structure to an extended position with the puncturing end extending through the forward opening, and to return to the relaxed condition retracting the puncturing end back within the housing.

28 Claims, 7 Drawing Sheets

(56) References Cited

U.S. PATENT DOCUMENTS

| | | | |
|---|---|---|---|
| 7,160,313 B2 * | 1/2007 | Galloway et al. | 606/167 |
| 7,244,265 B2 * | 7/2007 | Freeman et al. | 606/181 |
| 2003/0130597 A1 | 7/2003 | Marshall | |
| 2006/0052809 A1 | 3/2006 | Karbowniczek | |
| 2006/0129173 A1 | 6/2006 | Wilkinson | |

* cited by examiner

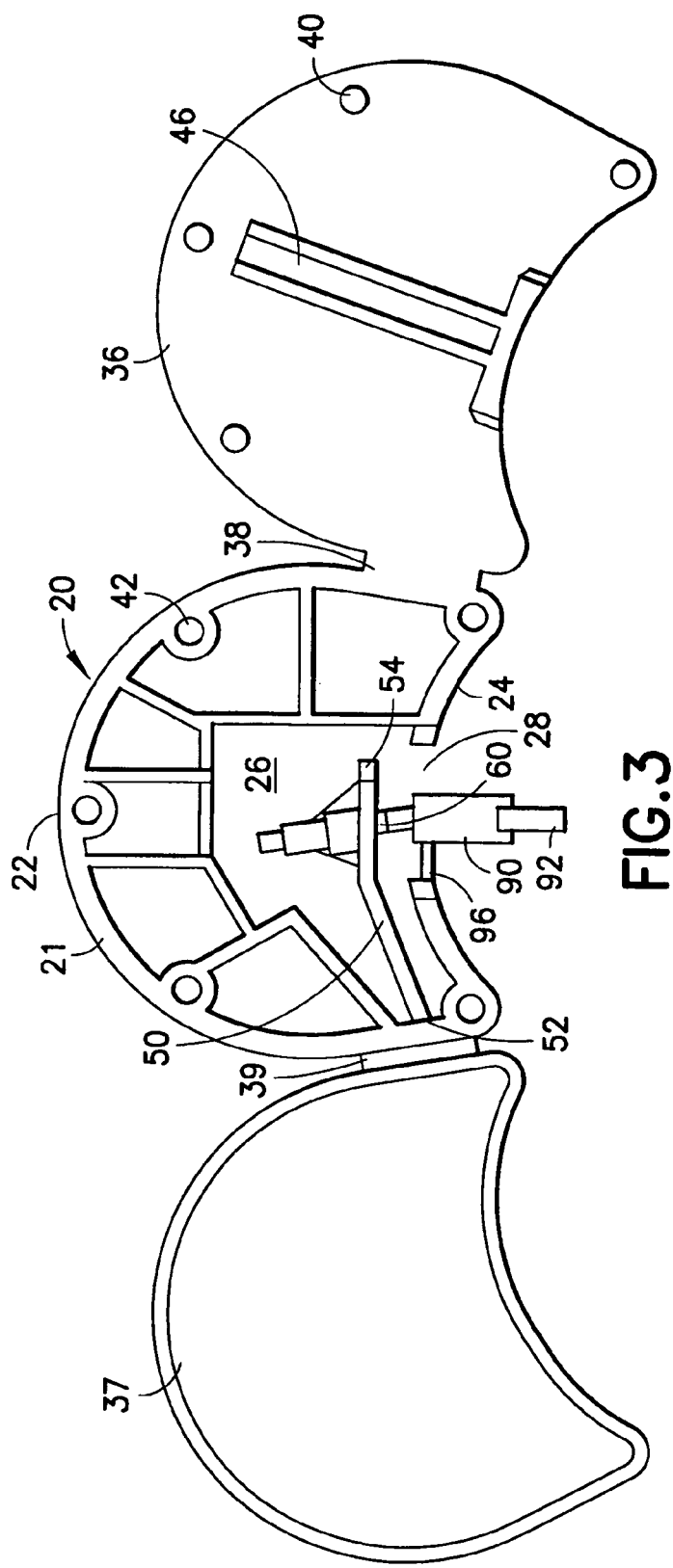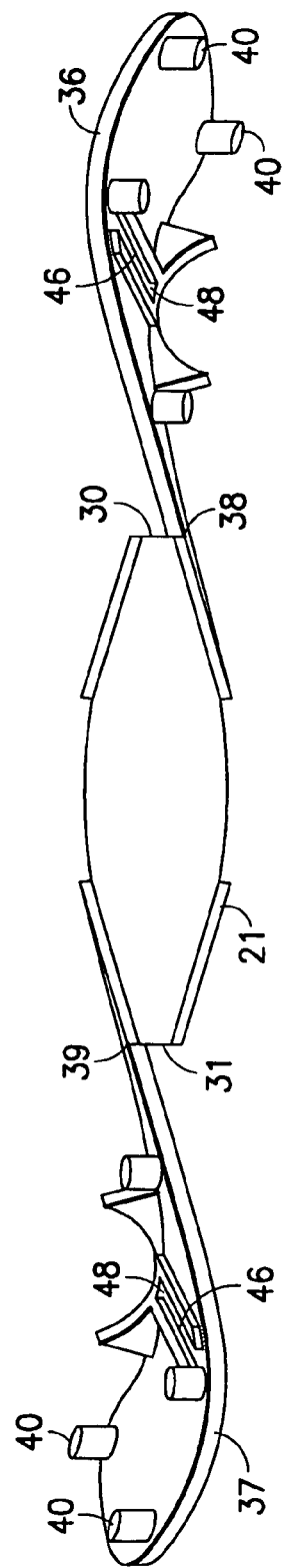

FINGER ACTIVATED LANCET DEVICE

The present application claims the benefit of U.S. Provisional Patent Application No. 60/669,248 as filed on Apr. 7, 2005.

BACKGROUND OF THE INVENTION

1. Field of the Invention

The present invention relates generally to medical puncturing devices, and more specifically to lancets which are used to take blood samples from patients.

2. Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example, on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design involves preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Examples of such medical puncturing devices are disclosed in U.S. Pat. Nos. 5,755,733; 6,432,120; and 6,248,120. U.S. Pat. No. 5,755,733 to Morita discloses a lancet device that includes a combined holder and lancet structure with a compressible zig-zag spring member that causes a lancet member to puncture the skin of a patient upon actuation of a pair of actuating arms. U.S. Pat. No. 6,432,120 to Teo discloses a lancet device including a lancet holder which contains a spring-loaded lancet structure with a single coil spring that effects the ejection and retraction of a lancet needle upon triggering of the structure. U.S. Pat. No. 6,248,120 to Wyszogrodzki discloses a lancet device comprised of a housing, a shielding portion, a piston with a puncturing tip, and separate drive and return coil springs that eject and retract the piston, respectively, upon the breakage of internal wing elements in the housing. Such assemblies include many components, and oftentimes utilize costly metal coil springs for activation.

U.S. Pat. No. 4,869,249 to Crossman et al. discloses a disposable lancet pricker having a body, a lance and an integrally molded zig-zag spring, which is activated by a separate cap inserted into the body. The zig-zag spring extends from the inner rear surface of the body to attach with the lance, and when compressed and released, causes the lance to project from and then retract back into the device. After use, the cap attaches with the lance to prevent further activation.

U.S. Pat. No. 6,136,013 to Marshall et al. discloses a lancet device formed from an integrally molded structure in a folded-out configuration. The device includes a two-part hinged housing with a button molded into one housing part and with a zig-zag spring hinged to the other housing part at the rearward end, with a lancet molded to the spring. The spring and lancet can be folded into the housing with the spring compressed, with the housing then closed to form the enclosed lancet. Activation is accomplished by laterally pushing the side button into the housing to release the compressed spring.

U.S. Pat. No. 5,630,828 to Mawhirt et al. discloses a disposable lancet having a housing, with a beam having a blade extending from one end and with the other end pivotally coupled to the housing. A trigger extends from a rear end into the housing, with activation involving pushing the trigger down into the housing to force the blade at the end of the beam spring to puncture the patient's skin, at which time the trigger is released to allow the beam spring to retract the blade back within the housing. Such a lancet involves the force of the user to puncture the skin, with the spring resulting in retraction of the lance.

SUMMARY OF THE INVENTION

A need generally exists in the medical field for a simple, inexpensive, reliable, and disposable medical puncturing device that is easy to manufacture, assemble and use, and which ensures sterility before use and enables safe and secure disposal after use.

A lancet device comprises a housing including a forward opening, and a flexible member, such as a cantilever spring, extending within the housing, such as from an inner wall thereof. A lancet structure with a puncturing end is provided in communication with the flexible member, and may be directly attached adjacent an end of the flexible member. The flexible member is adapted to pivot the lancet structure between a retracted position in which the puncturing end of the lancet structure is maintained within the housing and an extended position in which the puncturing end extends through the forward opening. The lancet device further comprises an actuator which extends through the forward opening of the housing and contacts the flexible member through an engagement with the flexible member. The actuator is movable from a first position extending through the forward opening of the housing to a second position further within the housing, at least partially within the housing. Movement of at least a portion of the actuator releases the engagement between the actuator and the flexible member, thereby permitting the flexible member to pivot the lancet structure to the extended position.

Desirably, an end of the flexible member is integrally molded with a side wall of the housing, and the lancet is adjacent the opposing end of the flexible member, thereby establishing the flexible member as a beam or a cantilever, which can pivot about a pivot point established at the engagement of the flexible member and the inner housing wall. The lancet structure may also be integrally molded with the flexible member, desirably with the lancet insert molded therein. Further, the lancet structure, the flexible member, and the housing may all be integrally molded as a single structure.

The actuator may be in the form of a generally hollow shield including an internal extension for engagement with the cantilever spring, such as an internal finger which contacts the end of the cantilever spring. The actuator may be a structure which is independent of the housing. The cantilever spring desirably maintains the puncturing end of the lancet within the housing when the cantilever spring is in a relaxed condition. In this manner, initial movement of the actuator within the housing from the first position toward the second position causes the engagement with the cantilever spring to pivot the cantilever spring against its relaxed condition, and continued movement of the actuator within the housing to the second position releases the engagement with the cantilever spring. As such, the cantilever spring pivots beyond its relaxed condition to extend the lancet structure to the extended position and to subsequently return to its relaxed condition, thereby retracting the lancet structure to the retracted position.

Desirably, the forward opening of the housing is generally medial with respect to a forward portion of the housing. In this manner, activation of the lancet device is accomplished with a downward movement at the central or medial portion of the device.

In a further embodiment of the invention, a lancet device comprises a housing including a housing wall defining an interior cavity and including a forward opening through the forward end thereof, with a cantilever spring extending from the housing wall within the interior cavity. The cantilever spring includes a lancet structure comprising a puncturing end, and the cantilever spring is adapted to pivot the lancet structure between a retracted position in which the puncturing end is maintained within the housing and an extended position in which the puncturing end extends through the forward opening. An actuator extends through the forward opening of the housing for interfering engagement with the cantilever spring. The actuator is movable through the forward opening of the housing into the interior cavity to a position in which the actuator is released from engagement with the cantilever spring, thereby permitting the cantilever spring to pivot the lancet structure to the extended position. Desirably, the housing is integrally molded with hinged side walls which hinge to a closed position, enclosing the cantilever spring with the lancet structure within the housing.

In a further embodiment, a lancet device for puncturing the skin of a patient comprises a housing body defining an interior cavity and including a forward opening therethrough, with a cantilever spring in pivotable engagement with the housing body at a pivot point and including a lancet comprising a puncturing point extending within the interior cavity. Pivotal movement of the cantilever spring about the pivot point moves the lancet between a retracted position in which the puncturing point is maintained within the housing body and a puncturing position in which the puncturing point extends through the forward opening of the housing body. The pivot point of the cantilever spring is substantially aligned in a plane defined by the position of the puncturing point of the lancet when in the puncturing position. An actuator is movably associated within the forward opening of the housing body and includes a forward end for contact with the skin of a patient during a puncturing procedure. The actuator also engages the cantilever spring. In this manner, movement of the actuator into the forward opening of the housing body releases the engagement with the cantilever spring, thereby permitting the cantilever spring to pivot the lancet structure to the extended position. Desirably, the cantilever spring comprises a first end fixed to the housing body to define the pivot point and a second end extending into the interior cavity, with the lancet positioned adjacent the second end. The pivot point may be positioned within the housing in alignment with the puncturing point of the lancet when in the puncturing position to define a plane which is substantially coplanar to a plane defined by the forward end of the actuator.

In another embodiment, a lancet device comprises a housing including a housing wall defining an interior cavity and including a forward opening through the forward end thereof, with the housing including a cantilever spring extending from the housing wall within the interior cavity. The cantilever spring includes a puncturing end and is adapted to pivot the lancet structure between a retracted position in which the puncturing end is maintained within the housing and an extended position in which the puncturing end extends through the forward opening. A lancet cover is integrally molded with the housing. An actuator extends through the forward opening of the housing and engages the cantilever spring. The actuator is retractably movable through the forward opening of the housing into the interior cavity to a position in which the actuator is released from engagement with the cantilever spring. The lancet cover as molded with the housing is adapted to protect the puncturing tip before and after the actuator has been assembled at least partially inside the housing.

BRIEF DESCRIPTION OF THE DRAWINGS

FIG. 3 is side view of the outer housing of the lancet device of FIG. 1 shown in a pre-assembled state.

FIG. 4 is a top view of the outer housing of FIG. 3.

DESCRIPTION OF THE PREFERRED EMBODIMENTS

Figure 1:
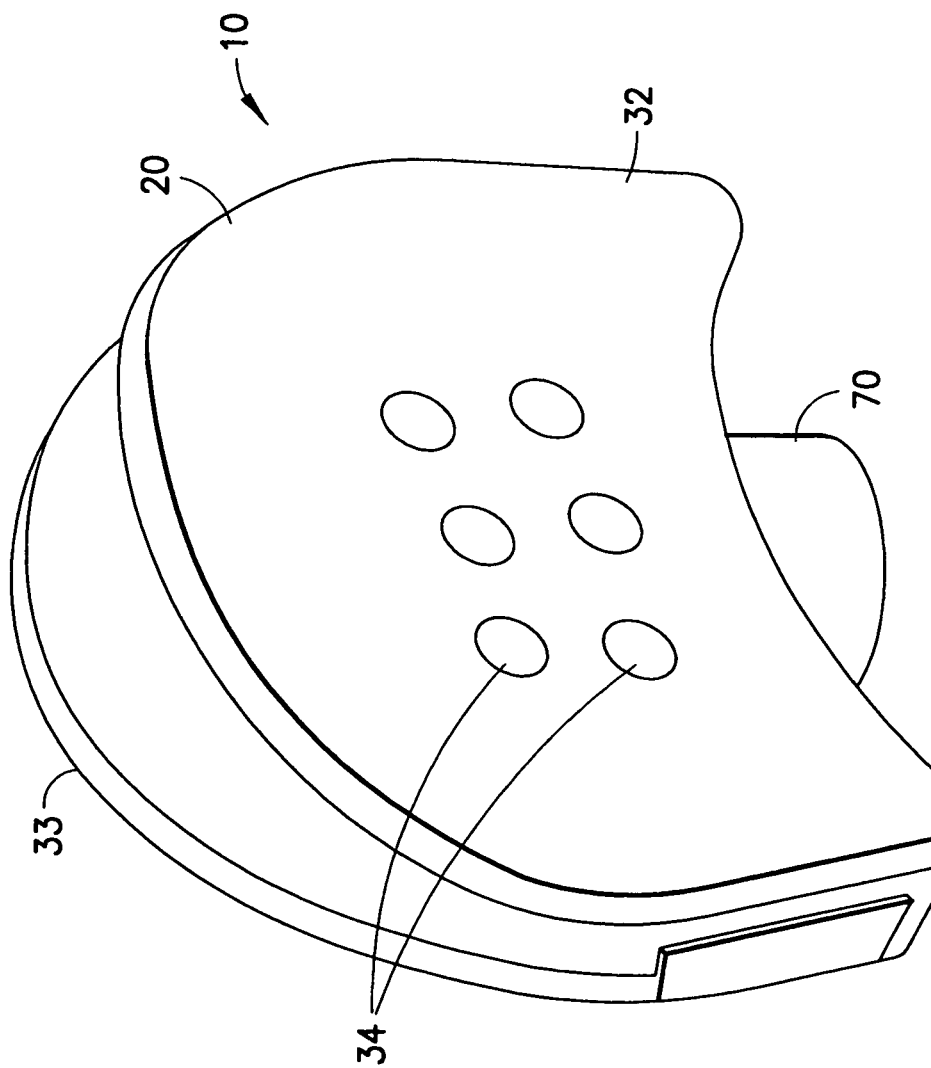
FIG. 1 is perspective view of a lancet device in accordance with an embodiment of the present invention.

For purposes of the description hereinafter, the words "upper", "lower", "right", "left", "vertical", "horizontal", "top", "bottom", "lateral", "longitudinal" and like terms, if used, shall relate to the embodiments of the invention as oriented in the drawing figures. However, it is to be understood that the present embodiments of the invention may assume many alternative variations. It is also to be understood that the specific devices and embodiments illustrated in the accompanying drawings and described herein are simply exemplary embodiments of the invention.

Referring to FIGS. 1-4, a lancet device 10 according to one embodiment of the invention is generally shown. The lancet device 10 generally includes a main housing enclosure in the form of housing body 20 and an actuator element 70 movably associated therewith, and a lancet structure 60 disposed therein. As will be discussed in greater detail herein, the actuator 70 is movably associated with the forward end of the housing body 20, with the lancet structure 60 contained within and movable therethrough. A protective cover such as cover body 90 is further provided to ensure sterility of the lancet prior to use.

Figure 2:
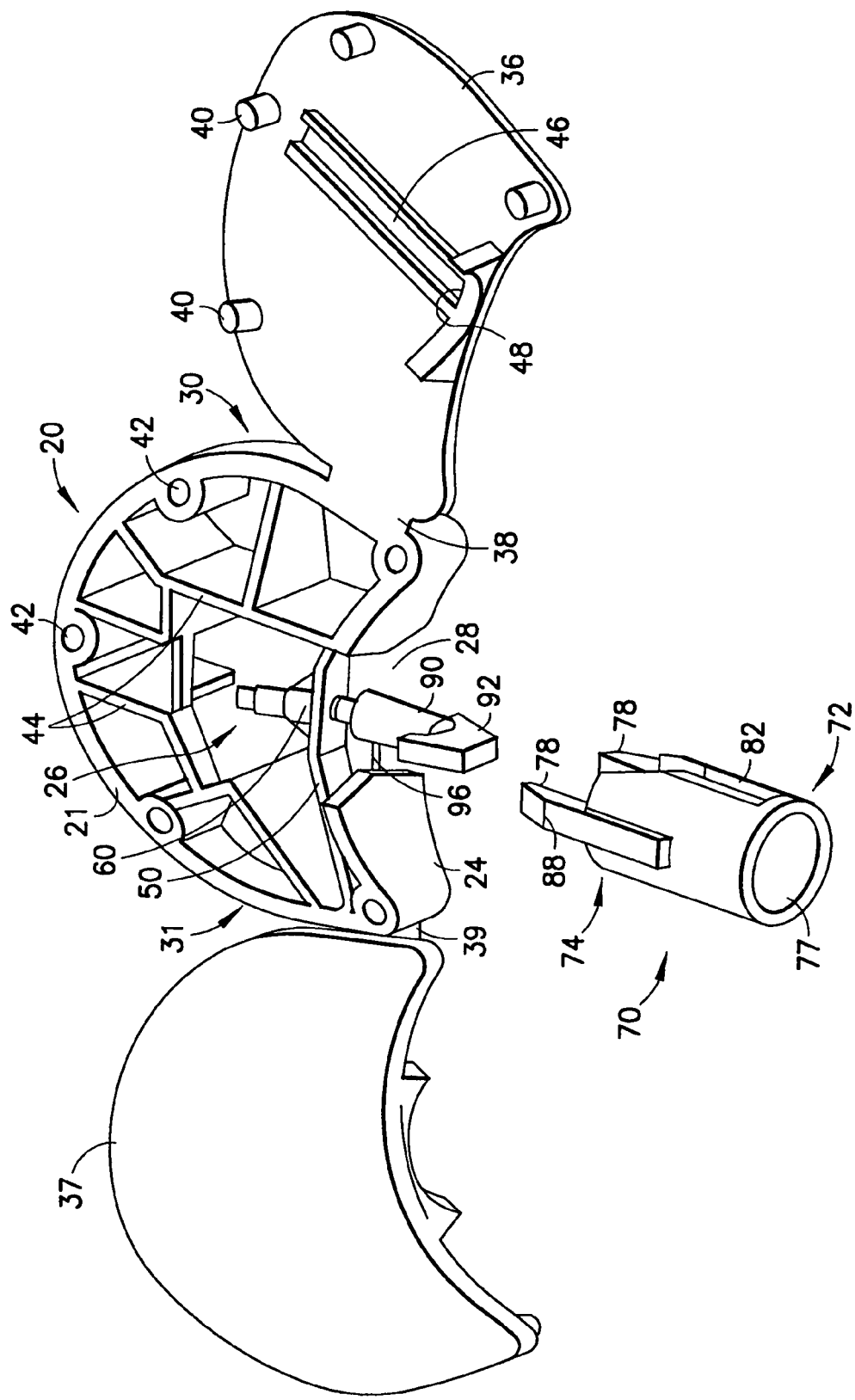
FIG. 2 is an exploded perspective view of the lancet device of FIG. 1.

The main housing includes a housing wall structure defining generally disc-shaped housing body 20 extending between a rearward end 22 and a forward end 24. Housing body 20 is a generally closed housing structure defining an interior cavity 26, with a forward opening 28 extending through the forward end 24 through which the lancet structure can extend, as will be discussed in further detail herein. In one embodiment as shown in FIGS. 1-3, the forward end 24 may include a concave-shaped profile for accommodating a patient's finger in a finger pricking procedure. As a generally disc-shaped structure, housing body 20 includes opposing narrow lateral sides 30, 31 as well as opposing generally flat lateral sides 32, 33. Desirably, forward opening 28 extends through the forward end 24 of housing body 20 at a generally medial position with respect to the forward end 24 of the housing.

The housing body 20 is desirably provided as a molded structure extending between the rearward end 22 and the forward end 24 to define the interior cavity 26 with forward opening 28. Housing body 20 is desirably molded as an open housing structure 21 with opposing lateral sides 32, 33 open and extending outwardly from housing body 20 in the form of flaps 36, 37 integrally molded to housing body 20 through living hinges 38, 39, respectively. Living hinges 38, 39 connect flaps 36, 37 to opposing lateral sides 30, 31 of housing body 20 in a hinged, bendable manner. As such, housing body 20 may be easily molded as a single structure with flaps 36, 37 open to assist in molding procedures. Additionally, housing body 20 may be formed with a plurality of struts and supports defining an interior support structure 44 within the interior cavity 26, thereby providing structural support for lancet device 10 and assisting in the molding process for housing body 20.

During assembly of lancet device 10, flaps 36, 37 can be pivoted about respective hinges 38, 39 to a closed position, thereby enclosing interior cavity 26 and providing housing body 20 as an enclosed structure. Flaps 36, 37 may be fixed in place with respect to housing body 20 in any known manner, such as through a mechanical engagement, an adhesive, or other known fixation methods. As shown in FIGS. 2 and 4, flaps 36, 37 may include a plurality of protrusions, such as pegs 40 spaced about the outer perimeter of flaps 36 and 37, and housing body 20 may include a plurality of corresponding recesses, such as openings or recesses 42 which correspond to each of the pegs 40. In this manner, when flaps 36 and 37 are closed during assembly, pegs 40 can be snap fit within the openings or recesses 42 in a snap fit engagement, thereby forming housing body 20 as an enclosed structure with lateral sides 32, 33 defining the enclosed interior cavity 26.

Housing body 20 may include a surface for accommodating a user's fingers. For example, housing body 20 may include ergonomically shaped surfaces for accommodating a user's finger, and may further include surface features for providing a tactile feel to the user, such as ribs, grooves, bumps, protrusions, or the like on the outer surface of the housing body 20, including bumps 34 on the outer surface of lateral sides 32, 33. Such features can aid the user in manipulating the lancet device 10 and using the lancet device 10 in a blood letting, drawing, or collection procedure, and may provide multiple finger grip positions for the user.

Figure 5:
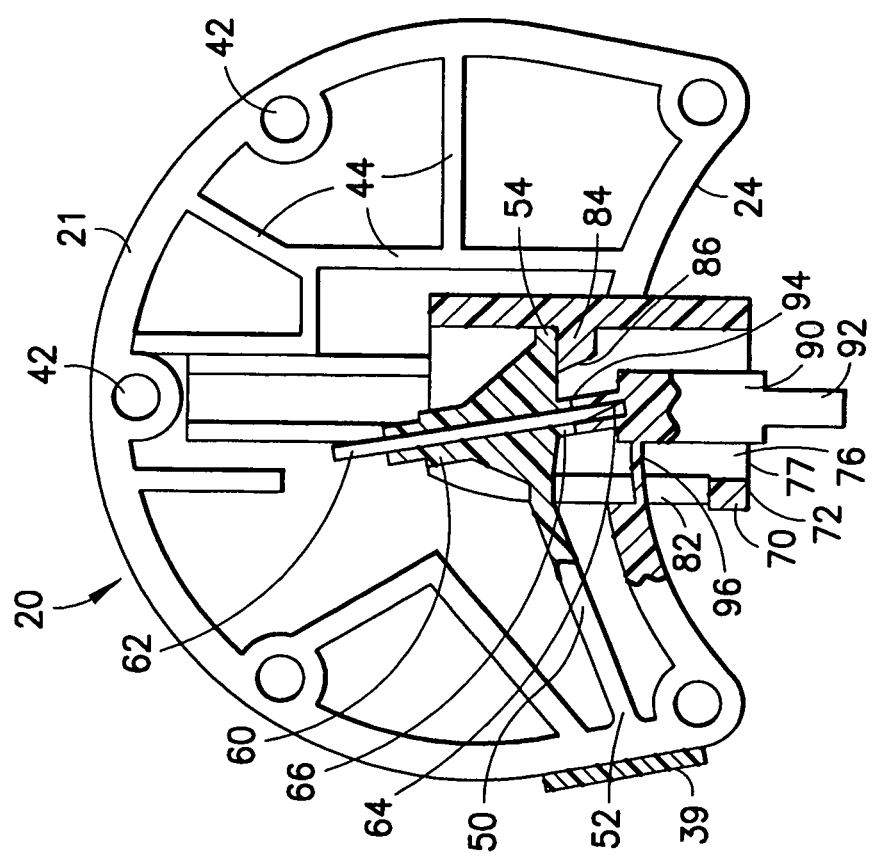
FIG. 5 is a side partial sectional view of the lancet device of FIG. 1.
Figure 6:
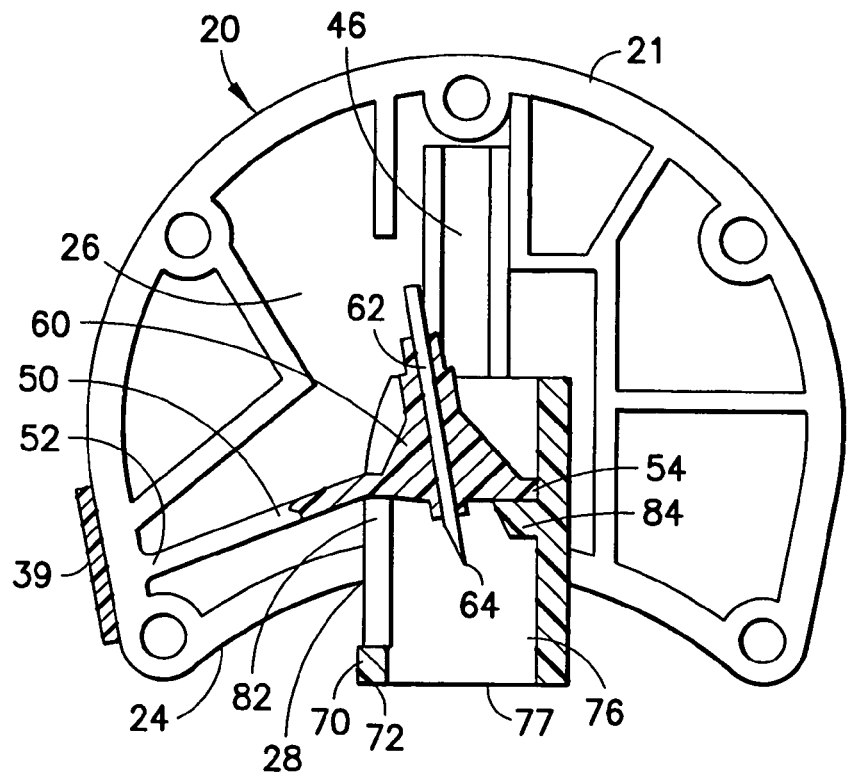
FIG. 6 is a side partial sectional view of the lancet device of FIG. 1 with the protective cover removed and ready for use.

Lancet device 10 further includes a lancet structure 60 disposed within the housing body 20. As shown in FIG. 5, lancet structure 60 includes a puncturing element, shown in the form of lancet 62 defining a puncturing end 64 at the forward end thereof. Lancet structure 60 is adapted for movement through the housing body 20 between an initial position with the puncturing end 64 maintained within the housing body 20 to a puncturing position in which the puncturing end 64 extends beyond the forward opening 28 of housing body 20, as will be discussed further herein in terms of use of the lancet device 10. Puncturing end 64 is adapted for puncturing the skin of a patient, and may define a pointed end, a blade edge, and the like. Puncturing end 64 may also include a preferred alignment orientation, such as with a pointed end of a blade aligned in a specific orientation. Lancet structure 60 may further include an elongated body, such as a carrier element 66 supporting lancet 62.

Lancet structure 60 is adapted to be moved through the housing body 20 to a puncturing position in which the puncturing end 64 of lancet 62 extends through the forward end 24 of housing body 20 through a spring mechanism. In particular, a flexible member or beam extends between the lancet structure 60 and the housing body 20, such as cantilever spring 50. Cantilever spring 50 is a simple beam spring extending between a first end 52 and a second end 54. Cantilever spring 50 may be manufactured, for example, from a flat bar or strip, and is supported at a first end 52 within the housing body 20 with the opposing second end 54 unrestricted with respect to housing body 20. Cantilevered spring 50 has a rigid integral connection with housing body 20 such that when second end 54 of cantilevered spring 50 when moved from an un-stressed position, a bending moment is established about the first end 52.

Cantilever spring 50 may be fixed or maintained at first end 52 within housing body 20. In particular, first end 52 and of cantilever spring 50 is in a fixed relationship within interior cavity 28 of housing body 20, such as by fixation to the interior surface of lateral side 30. Cantilever spring 50 may be insert molded, integrally molded, fixedly attached or otherwise adhered to housing body 20, such as through a mechanical frictional engagement or an appropriate adhesive. Desirably, cantilever spring 50 is integrally molded with housing body 20 through a conventional molding procedure, providing cantilever spring as a leaf-spring type of mechanism with sufficient resiliency and stiffness so as to provide the necessary force for driving the lancet structure 60 through the housing body 20, as will be discussed in further detail herein.

Cantilever spring 50 provides a mechanism for driving lancet structure 60 through housing body 20 to an extended position in which the puncturing end 64 of lancet 62 extends from housing body 20 to puncture the skin of a patient. Accordingly, lancet structure 60 and cantilever spring 50 are in a fixed relation, such that pivotal movement of the cantilever spring 50 results in corresponding movement of the lancet structure 60 through housing body 20. Cantilever spring 50 and lancet structure 60 may be separate structures which are attached together, or may be integrally molded, as shown in the embodiment of FIGS. 2-5, in which cantilever spring 50 is integrally molded with both lancet structure 60 and with housing body 20. In this manner, the cantilever spring 50 is adapted to provide the necessary driving force for driving the lancet structure 60 within the housing body 20 to the extended puncturing position. In the embodiment depicted in FIGS. 2-5, cantilever spring 50 represents a structure which includes a slight curve, and which is fixed to lateral side 30 of housing body 20 at first end 52 thereof and with lancet structure 60 integrally molded adjacent the second end 54 thereof.

Lancet device 10 further includes actuator 70 which extends outwardly from the forward end 24 of the housing body 20. As shown in FIG. 2, actuator 70 is a generally hollow structure extending between a forward end 72 and a rearward end 74 to define an interior channel 76 having an opening 77 at the forward end thereof, through which the puncturing element extends when the lancet device 10 is actuated by the user, as will be discussed in more detail herein. Actuator 70 may include a generally cylindrical profile which defines a small contact area about the opening 77 for contacting the intended area on the user's body which is to be punctured by the puncturing element.

Actuator 70 extends through forward opening 28 of housing body 20 and into the interior cavity 26 thereof. The actuator 70 is moveable within and into housing body 20. The housing body 20 and the actuator 70 may therefore include corresponding guiding surfaces for guiding the actuator 70 axially through the housing body 20. For example, actuator 70 may include one or more guide tabs 78 on opposing sides thereof, and housing body 20 may include one or more corresponding guide channels 46 on the interior surface walls of lateral sides 32, 33. Such corresponding guiding surfaces ensure that the actuator 70 is properly aligned within housing body 20, and further provide for sliding movement of the actuator 70 within the housing body 20, desirably preventing or resisting rotational movement. Additionally, housing body 20 and actuator 70 may include corresponding structure for interference engagement therebetween to prevent actuator 70 from sliding completely out of housing body 20. For example, one or more of the guide tabs 78 of actuator 70 may include a forward lip surface 80 for interfering or abutting engagement with the forward shoulder edge 48 of guide channel 46, thereby locking actuator 70 within housing body 20.

In one embodiment, actuator 70 is axially moveable within and into the forward opening 28 of housing body 20 in a direction aligned with the general axis of housing body 20, which is substantially perpendicular to the patient's skin surface. It is contemplated that actuator 70 may be moveable within and into the housing body 20 through forward opening 28 in a curved trajectory, such as shown and described further herein with reference to FIG. 10. Such a curved trajectory of movement may also be referenced as an axial movement herein, in that the initial movement if the actuator into the housing involves an axial movement, although such movement may transfer to such a curved movement.

Actuator 70 includes side openings 83 extending through the wall of actuator 70 for accommodating a portion of cantilever spring 50 therethrough. In this manner, with actuator 70 inserted through forward opening 28 of housing body 20, cantilever spring 50 can extend through actuator 70, with lancet structure 60 extending adjacent the second 54 of cantilever spring 50 maintained within the general interior channel 77 of actuator 70.

Actuator 70 acts as a lancet retention member for maintaining the puncturing end 64 of lancet structure 60 in a pre-actuated position within the housing body 20. For example, actuator 70 may include specific structure which is in interference engagement with the cantilever spring 50, thereby maintaining cantilevered spring 50 and lancet structure 60 associated therewith within the housing body 20. Such structure may be in the form of an internal structure extending within interior channel 77 of actuator 70, such as extension finger 84 extending radially inward into interior channel 77 from the interior surface of the wall of actuator 70. Extension finger 84 interferingly engages with the second end 54 of cantilever spring 50 in a releasable engagement, so as to maintain cantilever spring 50 in a predetermined position within housing body 20, thereby also maintaining the puncturing end 64 of lancet structure 60 associated with the second end 54 in the retracted position within housing body 20. Extension finger 84 may further include a sloped surface 86, over which the tip of second end 54 of cantilever spring 50 can ride when it is released from interference engagement with extension finger 84 during activation of the lancet device 10.

As noted, cantilever spring 50 provides lancet device 10 with the appropriate force required to drive lancet structure through housing body 20 and through actuator 70 to an extended puncturing position in which the puncturing end 64 extends from lancet device 10. Accordingly, cantilever spring 50 may be maintained in position within housing body 20 by the interference engagement with actuator 70 in a condition in which it is at least partially biased against its natural or relaxed state, thereby storing potential energy for pivotal driving movement of lancet structure 60. Such interference engagement between actuator 70 and cantilever spring 50, such as that established by extension finger 84 and the second end 54, may be a mere interference engagement which is releasable upon sliding movement between the respective elements, or may be a fracturable connection which fractures or breaks upon relative movement of the actuator 70 with respect to the housing body 20. In any event, upon the point of release of the interference engagement between actuator 70 and cantilever spring 50, cantilever spring 50 should be sufficiently biased and should store sufficient energy so as to drive lancet structure 60 through housing body 20 to a position at which puncturing end 64 extends through forward opening 28 of housing body 20 and forward opening 77 of actuator 70 and punctures the skin of the patient.

In one embodiment of the present invention, cantilever spring 50 maintains the puncturing end 64 of lancet 62 shielded within the housing body 20 when the cantilever spring is in a relaxed condition. More particularly, cantilever spring 50 may be designed such that in a relaxed or natural condition, cantilever spring 50 extends within interior cavity 26 in such a manner so as to retain the puncturing end 64 of lancet structure 60 in the retracted position within housing body 20. Desirably, lancet device 10 is designed such that in a pre-actuated state, cantilever spring 50 is partially biased against its natural or relaxed condition, and maintained in this position by way of the interference engagement provided through extension finger 84 and second end 54. During actuation of lancet device 10 through axial movement of actuator 70, cantilever spring 50 is further biased against its natural or relaxed condition until the interference engagement is released, at which point the cantilever spring 50 can pivotally drive the lancet structure 60 and subsequently retract the lancet structure 60, as will be described more fully in terms of use of the device.

Figure 8:
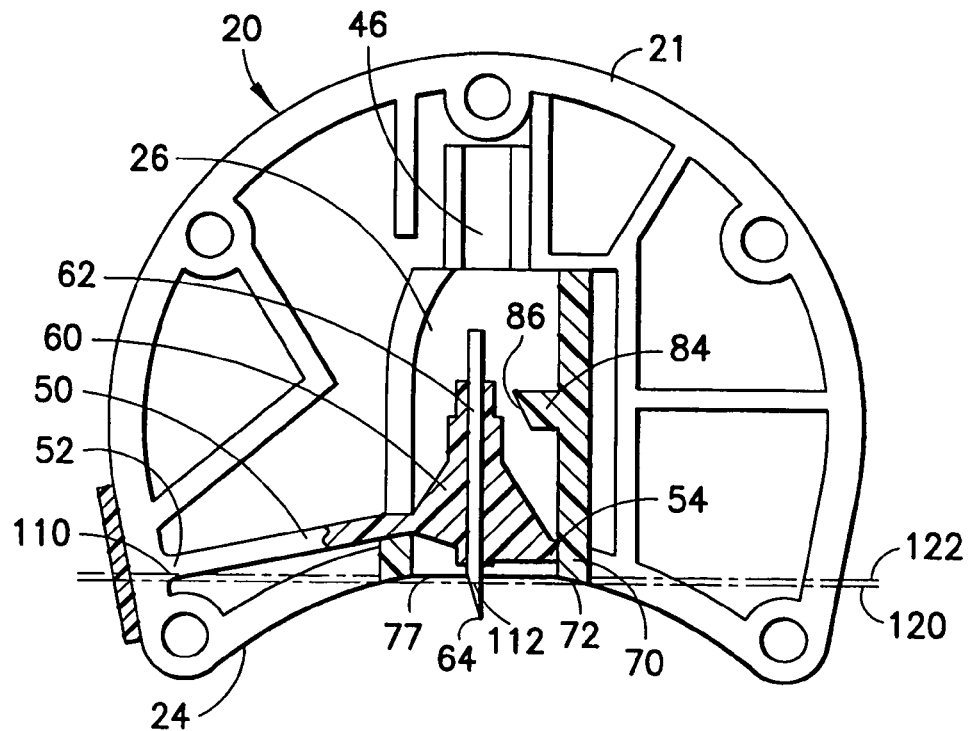
FIG. 8 is a side partial sectional view of the lancet device of FIG. 1 in use with the lancet structure in the puncturing position.

As noted, cantilever spring 50 may be in pivotal engagement with housing body 20 to provide for a pivotal movement of cantilever spring 50 upon actuation thereof, such as through a pivot point 110 established near the position of engagement between cantilever spring 50 and housing body 20. Such pivotal movement of cantilever spring 50 establishes an arc of travel for lancet 60. Moreover, as shown in FIG. 8, as puncturing end 64 extends beyond the forward opening 28 through the arc of travel of lancet 60, it begins to puncture through a patient's skin at an initial puncturing stage, and continues on a path into and through the patient's skin to a final puncturing stage. The path of travel or trajectory between this initial puncturing stage and this final puncturing stage defines a small path of travel. Since the travel of puncturing end 64 is based on the pivotal movement of cantilever spring 50, this travel defines a small arc of travel, with center point 112 defining the center of this arc of travel between the initial puncturing stage and the final puncturing stage. Pivot point 110 is substantially aligned with the puncturing end 64 of the lancet 62 when the puncturing end 64 is at the center point 112 of the arc of travel to define a plane 120 which is substantially perpendicular to a tangent of this arc of travel at the center point 112. Moreover, forward end 72 of actuator 70 defines a plane 122 against which a patient's skin surface is pressed during a puncturing procedure. The pivot point 110 may be positioned on housing body 20 at a location such that plane 120 is substantially coplanar with plane 122, i.e., is aligned within about 20 percent margin of error of parallel alignment. In this manner, the arc of trajectory of puncturing end 64 between the initial puncturing stage and the final puncturing stage is made to be as vertical as possible with respect to lancet 60. In other words, the plane defining the pivot point 110 and the center point 112 of the arc of travel is made to be as close as possible to perpendicular to lancet 60. In this manner, patient discomfort is minimized due to the minimal curvature of the trajectory of puncturing end 64 through the arc of travel within the patient's skin between the initial puncturing stage and the final puncturing stage. As depicted in FIG. 8, this may be accomplished by providing the forward end 24 of housing as an arcuate surface that can hug and/or wrap the skin surface such that with the housing positioned against the skin at a point at which the needle is in the puncturing position, a side portion of the housing body 20 at the forward end 24 extends below the point of contact with the patient's skin, and by positioning pivot point 110 low within the housing toward the forward end 24 at such a side portion.

It is noted that reference within the present disclosure to the puncturing end of the lancet being maintained within the housing body is intended to encompass any shielding arrangement of the puncturing end of the lancet, such as by way of the puncturing end of the lancet being shielded within the internal channel within the actuator element.

Moreover, lancet device 10 may include structure so as to prevent actuator 70 from moving out of housing body 20 after it has moved therein. This may be accomplished by providing specific structure which interferes to prevent a reverse movement of actuator 70. For example, lancet device 10 may include an interference engagement between actuator 70 and housing body 20, such as a ratchet-like interference engagement. In one embodiment, actuator 70 may include a protrusion 88 (which, in this instance, is formed by the upper portion of guides 78) for interference engagement with a corresponding structure such as stop 49 within guide channel 46, to provide a locking engagement therebetween, preventing a return movement of actuator 70 out of housing body 20.

Lancet device 10 may further include a protective cover 12 for protectively covering the puncturing end 64 of the lancet structure 60 prior to use thereof in order to maintain sterility. The protective cover 12 defines a cover body 90 which may extend within the opening 77 of the actuator 70, thereby protectively surrounding and encompassing at least a portion of the puncturing element, namely lancet 62. A tab 92 may extend from the cover body 90 beyond the opening 77 of the actuator 70. Cover body 90 is desirably formed integrally with carrier element 66 of lancet structure 60, completely encompassing lancet 62, thereby maintaining sterility thereof prior to use. Cover body 90 and carrier element 66 may include a notched portion 94 at a juncture therebetween, providing a fracture point for cover body 90 and for exposing lancet 62. Alternatively, the cover body 90 may be secured directly to the lancet 62 by methods customary in the medical field, such as with a releasable medical grade adhesive.

Alternately or in addition thereto, cover body 92 may include a fracturable or releasable connection 96 with the forward end 24 of housing body 20, which may be an integrally molded structure. In this manner, cover body 92 may be integrally molded directly with the housing body 20, to provide the housing with the lancet directly contained therein in a safe and secure manner prior to and during further assembly of the lancet device, with the cover providing further protection of the lancet until final use of the lancet device.

The respective elements of the lancet device may be formed, for example, of molded plastic material, such as a medical grade plastic material. The lancet 62 may be constructed of any suitable material adapted for puncturing the skin, and is typically a surgical grade metal such as stainless steel. The cantilever spring 50 may be constructed of any suitable material, such as a plastic or metallic material, and may be insert molded with the housing body 20 or may be integrally molded therewith. Desirably, the lancet device is assembled from two separate structures as depicted in FIG. 2, namely an integrally molded housing portion and a separate actuator to be inserted therein.

For example, as shown in FIGS. 2-4, the housing body 20 is desirably provided as a molded structure including the general housing structure 21 defining the rearward end 22, the forward end 24 and lateral sides 30 and 31, with internal support structure 44 molded within the interior cavity 26. Flaps 36 and 37 are integrally molded with lateral sides 30 and 31 of general housing structure 21 through respective living hinges 38 and 39. Additionally, cantilever spring 50 is also integrally molded with general housing structure 21 as an extension arm with first end 52 extending directly from the internal surface of lateral side 30. Lancet structure 60 is further provided as an integrally molded structure at the opposing second end 54 of cantilever spring 50, including the cover body 90 and tab 92 integrally molded thereover and extending through forward opening 28, with the cover body 90 also integrally molded with forward end 24 at forward opening 28.

Actuator 70 is molded as a separate structure, and can be inserted within the forward opening 28 of general housing structure 21 in a manner such that cantilever spring 50 extends through a side opening 82 of actuator 70. Actuator 70 is inserted therein to a point at which internal extension finger 84 of actuator 70 contacts and interferingly abuts with the second end 54 of cantilever spring 50. At this point, flaps 36 and 37 can be pivoted about the respective living hinges 38 and 39 with each of pegs 40 snap fit within the respective recesses 42. During pivoting of flaps 36 and 37, guide tabs 78 of actuator 70 are properly aligned with the corresponding guide channels 46 of the flaps 36, 37, to lock actuator 70 within housing body 20. With flaps 36 and 37 entirely closed, housing body 20 is formed with flaps 36 and 37 forming opposing lateral sides 32 and 33, thereby defining interior cavity 26 within housing body 20. Actuator 70 is held within housing body 20 through the abutting engagement of lip 80 within the end edge 48 of guide channel 46.

Use of the lancet device 10 will now be described with particular reference to FIGS. 5-9. Prior to use, lancet device 10 is provided as shown in FIGS. 1 and 5, with protective cover 12 covering lancet 62. Lancet device 10, and in particular lancet structure 60, is in an initial pre-activation state, with cantilever spring 50 held in a partially biased state against its natural relaxed condition through the interference engagement of second end 54 with extension finger 84, thereby maintaining puncturing end 64 of lancet structure 60 within housing body 20.

To prepare the lancet assembly for use, the user grasps housing body 20, such as between a finger and thumb on opposing lateral sides 32, 33, and removes the protective cover 12 from the forward end, thereby exposing the puncturing end 64 of lancet 62 within actuator 70 and within housing body 20. The tab 92 may be ergonomically formed to allow the user to easily manipulate the tab member 92 and apply the necessary force to break the cover body 90 from the carrier element 66 by breaking the connection at notch 94 and/or the connection 96 if provided, to thereby release the cover body 90 from the lancet 62. The applied breaking force is in accordance with the present invention and may be a singular twisting or pulling motion, or a combined "twisting" (i.e. rotational) and "pulling" motion applied for breaking the connection between the cover body 90 and the carrier element 66. The interference engagement of second end 54 of cantilever spring 50 with the extension finger 84 of actuator 70 prevents any activation of the lancet device 10 during removal of the protective cover 12 in this manner.

The forward end 72 of actuator 70 may then be contacted with a location on the skin surface of a user's body or another person's body where it is desired to initiate blood flow. If provided, target indicia on the lancet device 10 may be aligned with the desired location of puncture. As noted above, the forward opening 28 through which actuator 70 extends is located a generally medial position with respect to the forward end 24 of the housing body 20.

Once placed against the body, the user exerts a downwardly directed force on the housing body 20, forcing actuator 70 against the skin surface. In particular, the user applies a force against the rearward end 22 of housing body 20, thereby applying a force against the skin surface. With the forward opening 28 located at a generally medial position, the force required for activation can be properly directed in a downward manner, and centrally directed with the respect to housing body 20, regardless of the pivoting nature of the cantilever spring. Such force establishes an opposing external pressure force between the forward end 72 of the actuator 70 and the housing body 20, causing the actuator 70 to move within the housing body 20. The corresponding guiding surfaces provided through guide tabs 78 and guide channels 46 guide the actuator 70 through forward opening 28 and into the housing body 20, ensuring proper alignment therebetween.

Movement of the actuator 70 within the housing body 20, such as axial movement therein, causes the interference engagement provided through extension finger 84 to pivot cantilever spring 50 within housing body 20 toward the rearward end 22 thereof. More particularly, with cantilever spring 50 fixed at first end 52 with respect to housing body 20, and with extension finger 84 in interference engagement with the second end 54 of cantilever spring 50, movement of actuator 70 within housing body 20 causes cantilever spring 50 to pivot about a pivot hinge provided through the connection with the housing wall at first end 52. As actuator 70 continues to pivot cantilever spring 50, such pivoting causes cantilever spring 50 to store energy due to its resilient nature.

Figure 7:
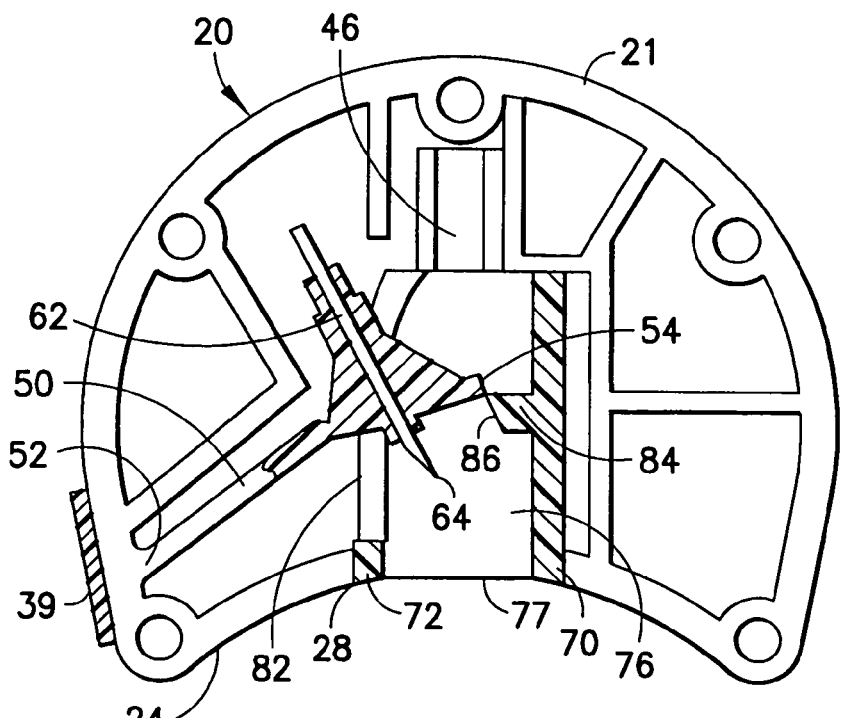
FIG. 7 is a side partial sectional view of the lancet device of FIG. 1 in use with the lancet structure in the primed position ready for release.

As shown in FIG. 7, continued movement of actuator 70 within housing body 20 causes continued pivoting of cantilever spring 50, which causes second end 54 to slide along the upper surface of extension finger 84 to a point at which it is released from interference engagement. At this point, the forward edge at the second end 54 of cantilever spring 50 rides along sloped surface 86 of the extension finger 84. The energy stored within cantilever spring 50 automatically causes cantilever spring to pivot about the pivot hinge provided through the connection with the housing wall at first end 52 in an opposite direction toward forward end 24 of housing body 20. Since lancet structure 60 is interconnected adjacent the second end 54 of cantilever spring 50, such pivoting movement drives the lancet structure 60 through the housing body 20 toward the forward end 24 and through forward opening 77 of the actuator 70 toward the skin surface to a puncturing position, in which puncturing end 64 of lancet 62 extends through the forward opening 77, as depicted in FIG. 8, a sufficient distance and with sufficient force to cause the puncturing end 64 to puncture the skin surface.

Figure 9:
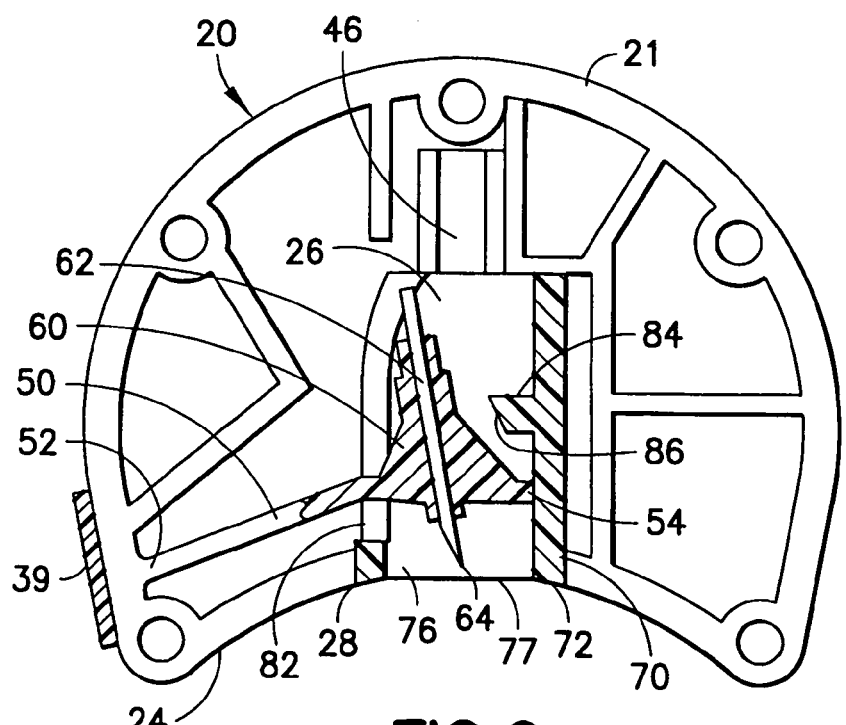
FIG. 9 is a side partial sectional view of the lancet device of FIG. 1 after use with the lancet structure in the final retracted position.

Such movement to the puncturing position causes cantilever spring 50 to pivot to a point at which it extends past its natural relaxed condition due to its resiliency. As such, when in the puncturing position, cantilever spring 50 is biased away from its relaxed condition, again storing return energy. Accordingly, immediately after achieving the puncturing position, the return energy stored in the cantilever spring 50 causes the cantilever spring 50 to pivot back to its relaxed condition. With lancet structure 60 interconnected with the cantilever spring 50, such return pivoting movement also causes lancet structure 60 to retract, with puncturing end 64 pulled back through the forward opening 77 of actuator 70 and the forward opening 28 of housing body 20 as shown in FIG. 9.

Moreover, the movement of actuator 70 within housing body 20 causes the protrusion 88 of actuator 70 to interferingly engage the stop 49 of housing body 20, thereby locking actuator 70 from further movement in or out of housing body 20. Such interaction locks the actuator 70 to the housing body 20, with lancet structure 60 retracted therein. The lancet device 10 is therefore safely protected from re-use and may be properly discarded, such as in an appropriate medical waste container.

Figure 10:
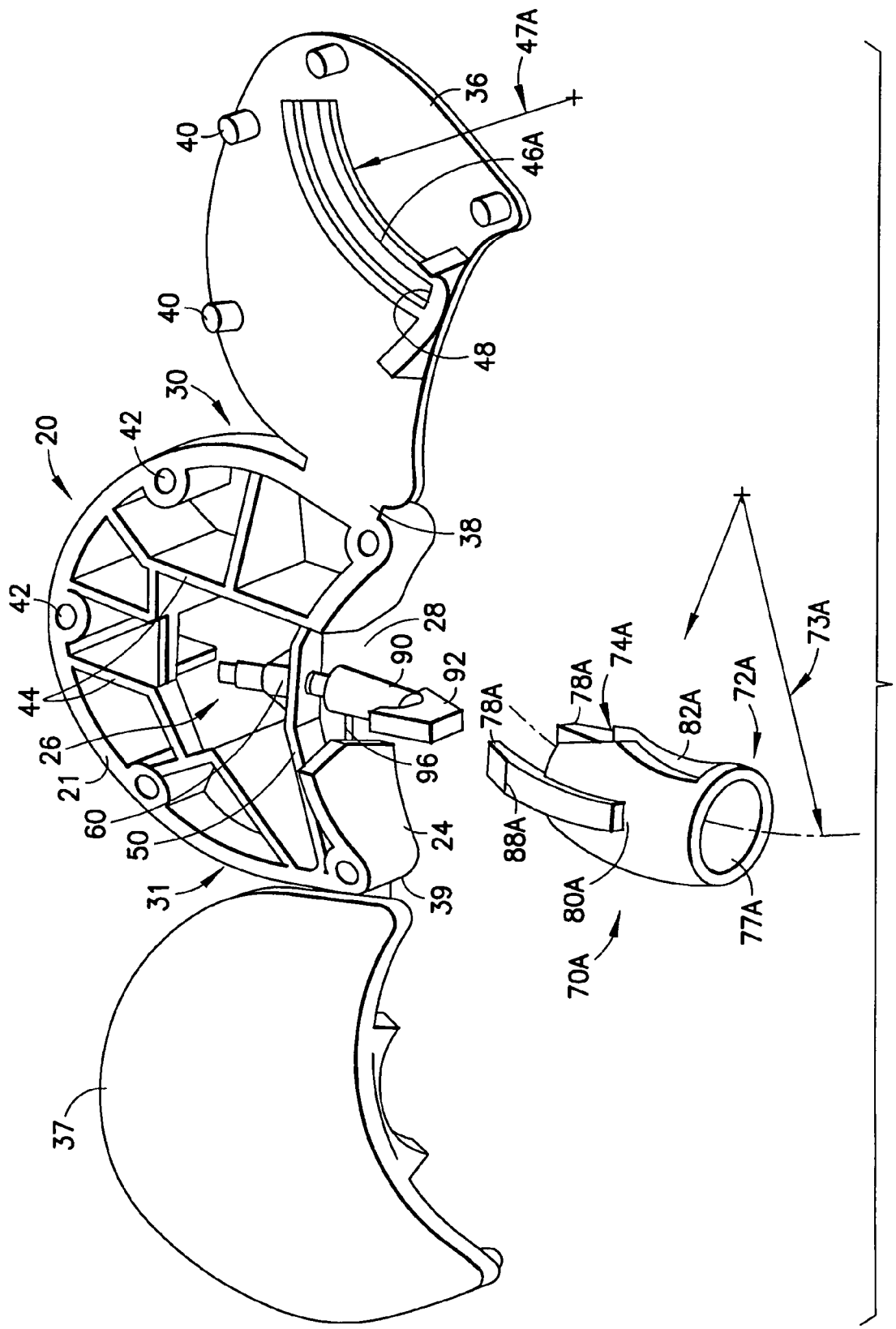
FIG. 10 is an exploded perspective view of a lancet device in a further embodiment.

FIG. 10 depicts a further embodiment of the invention that includes many components which are substantially identical to the components of FIGS. 1-9. Accordingly, similar components performing similar functions will be numbered identically to those components of FIGS. 1-9, and a suffix "a" will be used to identify those components in FIG. 10 which are similar but not necessarily identical to the previously described components.

In the embodiment of FIG. 10, actuator 70a is similar in design to actuator 70 discussed above, but includes a generally curved profile, defined by radius 73a. Actuator 70a extends between a forward end 72a and a rearward end 74a, with a forward opening 77a at the forward end 72a. Guide tabs 78a extend along opposing sides of actuator 70a, including a lip 80a at the forward edge thereof as well as a protrusion 88a. Actuator 70a further includes side openings 82a along the body thereof for accommodating the cantilever spring 50 of the housing body 20. Guide channels 46a are provided at one or both of lateral sides 32, 33, for accommodating guide tabs 78a of actuator 70a, and include a corresponding curved profile defined by radius 47a. In this manner, movement of actuator 70a within housing body 20 through forward opening 28a at forward end 24a thereof involves a slightly curved motion, albeit in the general axial direction of the lancet device. Such curved movement may further assist in disengagement of the cantilever spring 50 from actuator 70a, due to the actuator traveling in a curved movement in a direction away from the cantilever spring 50 extending within housing body 20.

While activation of the device is described herein in a stepwise fashion, it is noted that puncturing of the skin and retraction of the lancet occur almost instantaneously due to the design of the device and the tolerance of the materials. As such, while it is the actual pressure applied by the user which releases the engagement between the actuator and the cantilever spring, the retraction is based upon energy stored within the spring during movement to the puncturing position. Therefore activation of the device including piercing and retraction occur almost simultaneously in a single operation. The lancet device therefore provides an effective structure which may be safely protected from re-use.

While specific embodiments of the invention are described with reference to the figures, those skilled in the art may make modifications and alterations to such embodiments without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lancet device comprising:
a housing including a forward opening;
a lancet structure including a puncturing end;
a resiliently flexible member extending from an inner wall of the housing and connected with the lancet structure, the flexible member adapted to pivot the lancet structure between a retracted position in which the puncturing end is maintained within the housing and an extended position in which the puncturing end extends through the forward opening; and
an actuator extending through the forward opening of the housing and contacting the flexible member, the actuator including an engagement structure in contact with the flexible member, wherein at least a portion of the flexible member extends through a portion of the actuator to contact the engagement structure, the actuator being movable from a first position extending through the forward opening of the housing to a second position at least partially within the housing to store skin puncturing energy in the flexible member,
wherein movement of at least a portion of the actuator into the housing from the first position to the second position releases the engagement with the flexible member, thereby permitting the flexible member to pivot the lancet structure to the extended position to puncture the skin of a user.

2. The lancet device of claim 1, wherein a first end of the flexible member extends from a side wall of the housing forming a cantilever spring.

3. The lancet device of claim 2, wherein the lancet structure extends from the cantilever spring adjacent a second end of the cantilever spring opposite the first end.

4. The lancet device of claim 1, wherein the actuator comprises a generally hollow shield and the engagement structure comprises an internal extension for engagement with the flexible member.

5. The lancet device of claim 4, wherein the internal extension of the actuator interferingly engages with an end of the flexible member in a releasable engagement.

6. The lancet device of claim 1, wherein the flexible member maintains the puncturing end within the housing when the flexible member is in a relaxed condition.

7. The lancet device of claim 6, wherein initial movement of the actuator within the housing from the first position toward the second position causes the flexible member to pivot against its relaxed condition, and wherein continued movement of the actuator within the housing to the second position releases the engagement with the flexible member, thereby causing the flexible member to pivot beyond its relaxed condition to extend the lancet structure to the extended position and to subsequently return to its relaxed condition, thereby retracting the lancet structure to the retracted position.

8. The lancet device of claim 1, wherein the actuator and the housing include corresponding guiding surfaces for guiding the actuator within the housing.

9. The lancet device of claim 1, wherein the actuator and the housing include a locking engagement therebetween for preventing movement of the actuator within the housing after the actuator has been moved to the second position.

10. The lancet device of claim 1, further comprising a lancet cover removably covering the puncturing element of the lancet structure.

11. The lancet device of claim 1, wherein the lancet structure and the flexible member are molded as a single structure.

12. The lancet device of claim 1, wherein the lancet structure, the flexible member and the housing are molded as a single structure.

13. The lancet device of claim 1, wherein the actuator is independent from the housing.

14. The lancet device of claim 1, wherein the forward opening of the housing is generally medial with respect to a forward portion of the housing.

15. The lancet device of claim 1, wherein the actuator includes an opening through a sidewall configured to accommodate the portion of the flexible member extending therethrough.

16. A lancet device comprising:
a housing including a housing wall defining an interior cavity and including a forward opening through the forward end thereof, the housing including a resiliently flexible member extending from the housing wall within the interior cavity, the flexible member including a lancet comprising a puncturing end and being adapted to pivot the lancet between a retracted position in which the puncturing end is maintained within the housing and an extended position in which the puncturing end extends through the forward opening; and
an actuator extending through the forward opening of the housing and comprising an engagement structure engaging the flexible member, wherein at least a portion of the flexible member extends through a portion of the actuator to contact the engagement structure, at least a portion of the actuator being movable through the forward opening of the housing into the interior cavity to a position in which skin puncturing energy is stored in the flexible member and the actuator is released from engagement with the flexible member, thereby permitting the flexible member to pivot the lancet to the extended position to puncture the skin of a user.

17. The lancet device of claim 16, wherein the housing is integrally molded with hinged side walls which hinge to a closed position, enclosing the flexible member with the lancet within the housing.

18. The lancet device of claim 16, wherein the actuator comprises a generally hollow shield and the engagement structure comprises an internal extension for engagement with the flexible member.

19. The lancet device of claim 18, wherein the internal extension of the actuator interferingly engages with an end of the flexible member in a releasable engagement.

20. The lancet device of claim 16, wherein the flexible member maintains the puncturing end within the housing when the flexible member is in a relaxed condition.

21. The lancet device of claim 20, wherein initial movement of the actuator into the housing pivots the flexible member against its relaxed condition, and wherein continued movement of the actuator into the housing releases the flexible member, thereby causing the flexible member to pivot beyond its relaxed condition to extend the lancet to the extended position and to subsequently return to its relaxed condition, thereby retracting the lancet to the retracted position.

22. The lancet device of claim 16, wherein the flexible member is integrally molded with a side wall of the housing forming a cantilever spring.

23. The lancet device of claim 22, wherein the lancet extends from the cantilever spring adjacent an end of the cantilever spring opposite the end integrally molded with the side wall of the housing.

24. A lancet device comprising:
a housing including a forward opening;
a cantilever spring extending within the housing and including a lancet structure comprising a puncturing end, the cantilever spring adapted to pivot the lancet structure between a retracted position in which the puncturing end is maintained within the housing and an extended position in which the puncturing end extends through the forward opening; and
an actuator extending through the forward opening of the housing and contacting the cantilever spring, the actuator including an engagement structure in contact with the cantilever spring, wherein at least a portion of the cantilever spring extends through a portion of the actuator to contact the engagement structure, the actuator being movable from a first position extending through the forward opening of the housing to a second position at least partially within the housing,
wherein movement of at least a portion of the actuator within the housing from the first position to the second position stores skin puncturing energy in the cantilever spring and releases the engagement with the cantilever spring, thereby permitting the cantilever spring to pivot the lancet structure to the extended position to puncture the skin of a user.

25. A lancet device for puncturing the skin of a patient comprising:
a housing body defining an interior cavity and including a forward opening therethrough;
a cantilever spring in pivotable engagement with the housing body at a pivot point and including a lancet comprising a puncturing point extending within the interior cavity, such that pivotal movement about the pivot point moves the lancet between a retracted position in which the puncturing point is maintained within the housing body and a puncturing position in which the puncturing point extends through the forward opening of the housing body; and
an actuator movable within the forward opening of the housing body, the actuator including a forward end for engagement with the skin of a patient and including an engagement structure in contact with the cantilever spring wherein at least a portion of the cantilever spring extends through a portion of the actuator to contact the engagement structure, such that movement of the actuator into the forward opening of the housing body stores skin puncturing energy in the cantilever spring and releases the engagement with the cantilever spring, thereby permitting the cantilever spring to pivot the lancet to the extended position to puncture the skin of a user,
wherein the pivot point of the cantilever spring and the puncturing point of the lancet when in the puncturing position define a plane which is substantially coplanar to a plane defined by the forward end of the actuator.

26. The lancet device of claim 25, wherein the cantilever spring comprises a first end fixed to the housing body to define the pivot point and a second end extending into the interior cavity, and wherein the lancet is positioned adjacent the second end.

27. A lancet device comprising:
a housing including a housing wall defining an interior cavity and including a forward opening through the forward end thereof, the housing including a cantilever spring extending from the housing wall within the interior cavity, the cantilever spring including a puncturing end and being adapted to pivot the puncturing end between a retracted position in which the puncturing end is maintained within the housing and an extended position in which the puncturing end extends through the forward opening;
a lancet cover integrally molded with the housing; and
an actuator extending through the forward opening of the housing and comprising an engagement structure engaging the cantilever spring, wherein at least a portion of the cantilever spring extends through a portion of the actuator to contact the engagement structure, the actuator being retractably movable through the forward opening of the housing into the interior cavity to a position in which skin puncturing energy is stored in the cantilever spring and the actuator is released from engagement with the cantilever spring;
wherein the lancet cover is capable of protecting the puncturing end after the actuator has been disposed at least partially inside the housing.

28. The lancet device of claim 1, wherein the flexible member is in pivotal engagement with the housing at a pivot point, and the flexible member is adapted to pivot the puncturing end of the lancet structure through an arc of travel between the retracted position and the extended position, the arc of travel including a center point, the pivot point aligned with the puncturing end of the lancet structure with the puncturing end at the center point.

* * * * *